United States Patent

Ono et al.

[11] Patent Number: 4,971,965
[45] Date of Patent: Nov. 20, 1990

[54] ANTIBIOTICS TAN-1057

[75] Inventors: Hideo Ono, Kobe; Yasunori Funabashi, Suita; Setsuo Harada, Kawanishi, all of Japan

[73] Assignee: Takeda Chemical Industries, Ltd., Osaka, Japan

[21] Appl. No.: 344,391

[22] Filed: Apr. 28, 1989

[30] Foreign Application Priority Data

Apr. 29, 1988 [JP] Japan ................... 63-106733
Mar. 2, 1989 [JP] Japan ................... 1-051099

[51] Int. Cl.$^5$ .......... A01N 43/54; C12N 1/20; C07D 223/10; C07D 239/02
[52] U.S. Cl. .................. 514/218; 514/242; 435/252.1; 540/485; 544/320
[58] Field of Search .......... 540/485; 544/320; 514/218, 272; 435/252.1

[56] References Cited

U.S. PATENT DOCUMENTS

| | | | |
|---|---|---|---|
| 4,258,045 | 3/1979 | Poe et al. | 514/272 |
| 4,440,765 | 4/1981 | Diamond et al. | 514/218 |
| 4,478,839 | 10/1982 | Benneche et al. | 514/274 |
| 4,536,504 | 8/1985 | Okutani | 514/270 |
| 4,772,704 | 9/1988 | Algieri | 544/320 |

Primary Examiner—Ronald W. Griffin
Assistant Examiner—Pamela S. Webber
Attorney, Agent, or Firm—Wenderoth, Lind & Ponack

[57] ABSTRACT

Novel antibiotics TAN-1057 represented by the formula:

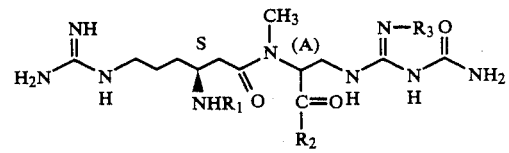

wherein, the absolute configuration at (A) is R or S; $R_1$ is hydrogen and both $R_2$ and $R_3$ taken together form a chemical bond, or $R_3$ is hydrogen and both $R_1$ and $R_2$ taken together form a chemical bond; were produced by microorganisms belonging to the genus Flexibacter. TAN-1057 strongly inhibit the growth of pathogenic microorganisms and malignant tumors, thus being useful as therapeutic agents of infectious diseases or antitumor agents.

7 Claims, 6 Drawing Sheets

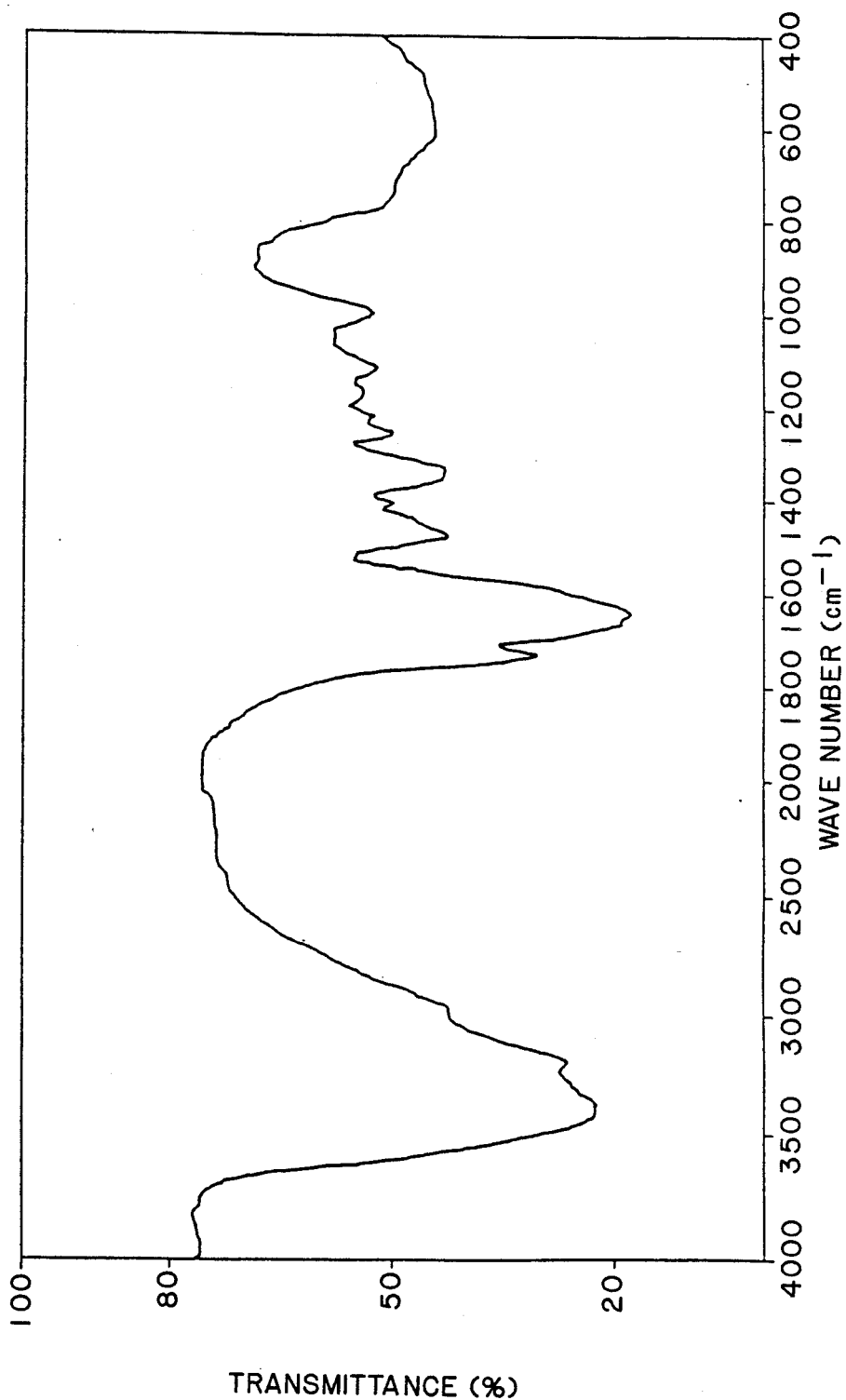

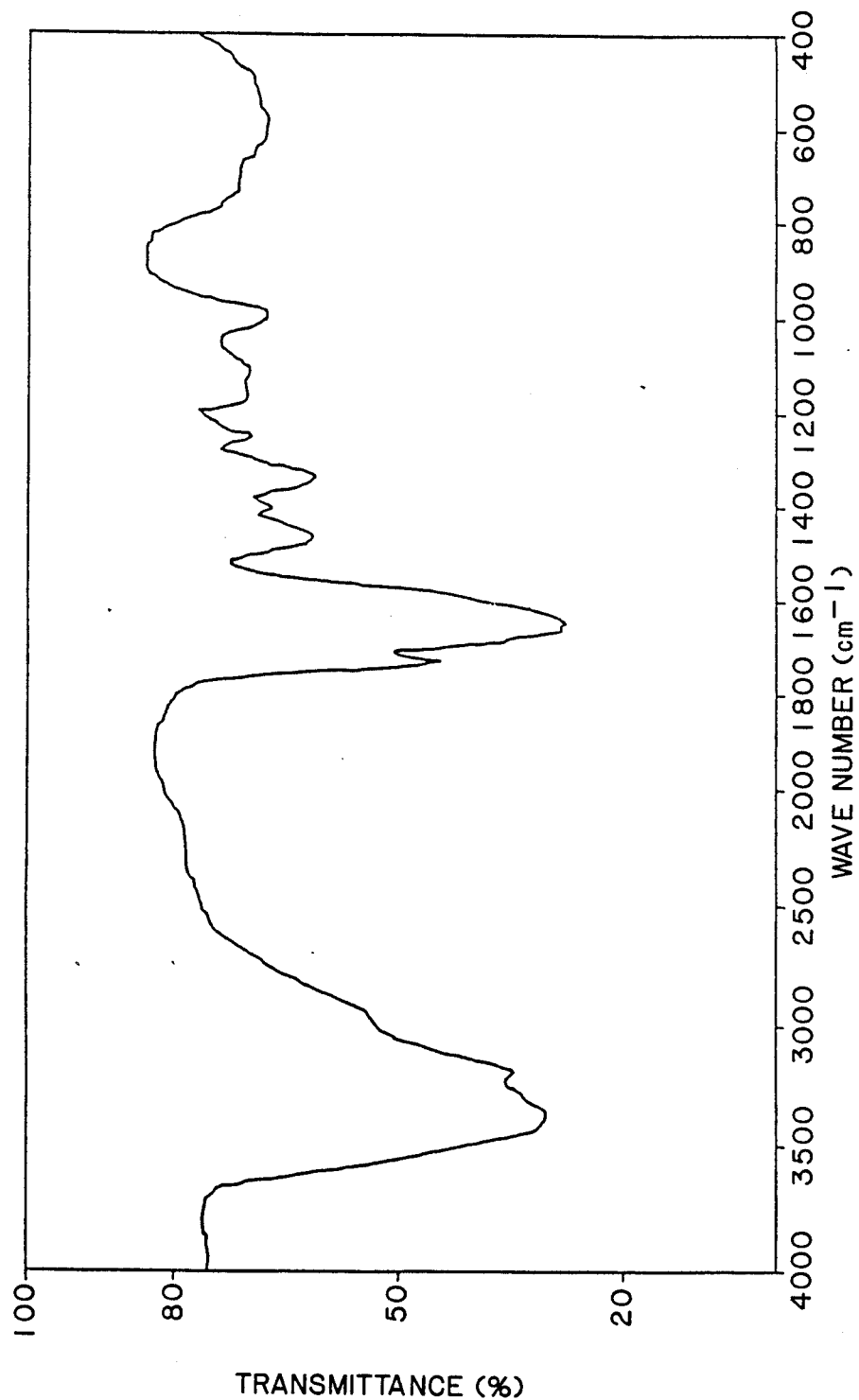

ANTIBIOTICS TAN-1057

This invention relates to novel antibiotics TAN-1057 useful as a therapeutic agent for infectious diseases caused by pathogenic microorganisms or an antitumor agent, production and use thereof.

Antibiotics TAN-1057 were compared with known antibiotic substances, and no relative or analogous compounds in chemical structure were found.

Owing to the development of therapeutics using antibiotics, diseases caused by bacteria have been overcome for the most part. There are, however, still some serious problems to be solved in the field of therapeutics of infectious diseases, for example, changes in the flora of disease-causative bacteria(replacement of bacteria) or advent of drug-resistant bacteria (acquisition of drug-resistance). Further, it is well known that effective agents against a malignant tumor are few. In order to solve these problems, in the field concerned, such substances as possessing novel structures and showing novel biological activities or intermediates for synthesizing them have incessantly been demanded.

The present inventors isolated a great number of bacterial strains from soils in search for new antibiotics and then separated and investigated antibiotics produced by them, finding that strains belonging to certain species produce new antibiotics, that these strains belong to the genus Flexibacter, and that these microbes are capable of accumulating in appropriate culture media antibiotics possessing antibacterial activity both gram-positive and gram-negative bacteria including resistant ones, spirochaeta, mycoplasma, etc. The present inventors isolated these antibiotics and, they confirmed that, on the basis of its physico-chemical and biological properties, these antibiotics were novel substances and decided to name them TAN-1057.

Based on these findings, the present inventors made further studies to complete the present invention.

The present invention provides (1) a compound of the formula [I]:

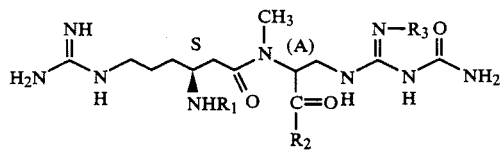

wherein, the absolute configuration at (A) is R or S; $R_1$ is hydrogen, and both $R_2$ and $R_3$ taken together form a chemical bond, or $R_3$ is hydrogen and both $R_1$ and $R_2$ taken together form a chemical bond; and salts thereof,
(2) a method for producing a compound of the formula [I], which comprises cultivating on a culture medium a microorganism belonging to the genus Flexibacter and capable of producing at least one species of compounds represented by said formula to allow at least one species of said compounds to be accumulated in the medium, recovering thus-accumulated product,
(3) an agent for treating infectious diseases, which contains at least one species of compounds represented by the formula [I], and
(4) an antitumor agent which contains at least one species of compounds represented by the formula [I].

In the present specification, "Antibiotics TAN-1057" is a general name of four compounds represented by the formula [I], and each compound is named as TAN-1057A, TAN-1057B, TAN-1057C and TAN-1057D according to the following designations:

TAN-1057A:
$R_1$ is hydrogen, both $R_2$ and $R_3$ taken together form a chemical bond, and the absolute configuration in (A) is S.

TAN-1057B:
$R_1$ is hydrogen, both $R_2$ and $R_3$ taken together form a chemical bond, and the absolute configuration in (A) is R.

TAN-1057C:
$R_3$ is hydrogen, both $R_1$ and $R_2$ taken together form a chemical bond, and the absolute configuration in (A) is R.

TAN-1057D:
$R_3$ is hydrogen, both $R_1$ and $R_2$ taken together form a chemical bond, and the absolute configuration in (A) is S. In the present specification, Antibiotics TAN-1057 are sometimes called simply "TAN-1057".

As the TAN-1057-producing microbes employable in the present invention, any ones belonging to the genus Flexibacter and capable of producing TAN-1057 can be mentioned, for example, PK-74 and PK-176 strains isolated from soil samples collected at Nachi-Katsuura-Cho, Higashi-Muro-Gun, Wakayama Prefecture, Japan and at Kamitsushima-Cho, Kamiagata-Gun, Nagasaki Prefecture, Japan respectively (hereinafter sometimes abbreviated as "PK-74 strain" and "PK-176 strain").

Taxonomical properties of PK-74 and PK-176 are as follows.

Strain PK-74

(a) Morphology

Morphological characteristics were observed after incubation on a bouillon-agar slant medium at 24° C. for 5 days.

Cell shape and size : Rod, 0.4 to 1.0 μm in diameter 0.9 to 1.2 μm in length, or filament, 20 to 40 μm in length
Fragella : None
Motility : Yes (gliding)
Sporulation : No
Formation of microcist : No
Gram-stain : Negative
Acid fastness : No
(b) Growth on various media Growth was observed on various media at 24° C. for 1 to 14 days.

1 Bouillon-agar plate culture:

Colonies are opaque, non-glossy, orange to pale brown, and circular. The colony surface is flat and the colony margin is sinuous.

2 Bouillon-agar slant culture:

Good unfolded cloth-like, orange to pale brown

3 Bouillon broth culture:

Grows in turbid suspension. Precipitation appears, but no formation of pellicle.

Bouillon gelatin stab culture:

Grows well mainly on upper portion. Crater-like liquefaction.

Litmus milk : Decolorization is observed.
(c) Physiological properties
1 Nitrate reduction: +
2 Denitrification: —
3 NM (methyl red) test : —
4 VP (Voges-Proskauer) test : —
5 Indole production : —

6 Production of hydrogen sulfide(TSI agar and lead acetate paper) : —
7 Starch hydrolysis : — ~ +(weak)
8 Citrate utilization(Koser's, Christensen's and Simon's medium) : +
9 Inorganic nitrogen source utilization :
   i) Potassium nitrate : —
   ii) Ammonium sulfate : +
10 Pigment production (King's A, King's B and Mannitol yeast extract agar medium) : No production of soluble pigment is observed in King's B medium. The pigment of mycelia was extracted with ethanol, which was subjected to determination of UV absorption in n-hexane. Maximum absorption was observed 425, 450 and 478 nm.
11 Urease : Oxidase
12 Oxidase : ±
13 Catalase : —
14 Temperatures for growing : 13 to 30.2° C., optimally 14° to 25.5° C. Medium : Bouillon liquid medium
15 Oxygen demand : Aerobic
16 O-F (oxidative-fermentation) test [Hugh Leifson method]: Not decomposed
17 Utilization of sugar : Utilizes D-glucose, D-mannose, D-galactose, maltose, trehalose, starch and cellobiose
18 Ability of decomposing polysaccharide :
   CMC :
   Colloidal chitin : — ~ ±
   Sodium arginate : — ~ ±
19 Hydrolysis of Tween 80 : —
20 Decarboxylation of amino acid :
   Ornithine : —; Arginine : —; Lysine : —
21 GC(guanine-cytosine) content in DNA : 33.4±1.0% (Tm method)

Strain PK-74 having the afore-mentioned taxonomical characteristics was collated with bacterial species described in Bergey's Manual of Determinative Bacteriology, 8th edition, International Journal of Systematic Bacteriology, Vol.30, pp.225 to 420(1980) and ibid Vol. 32, pp.146 to 149 to find that the strain was an orange-colored gram-negative rod having no flagella, showed motility by gliding and formed no spore and no microcist. Based on the following characteristics, i.e. the strain is aerobic, does not decompose high-molecular polysaccharide, and the GC content of its DNA is 33.4%, the strain was considered as bacteria belonging to the genus Flexibacter. Thus, PK-74 strain was considered as belonging to a species of the genus Flexibacter and decided to name it Flexibacter sp. PK-74.

Strain PK-176

(a) Morphology

Morphological characteristics were observed after incubation on a bouillon-agar slant medium at 24° C. for 5 days.
Cell shape and size : Rod, 0.4 to 1.0 μm in diameter 0.9 to 1.3 μm in length, or filament, 10 to 40 μm in length
Fragella : None
Motility : Yes (gliding)
Sporulation : No
Formation of microcist : No
Gram-stain : Negative
Acid fastness : No
(b) Growth on various media
Growth was observed on various media at 24° C. for 1 to 14 days.

1 Bouillon-agar plate culture:
   Colonies are semi-opaque, glossy, cream, and circular. The colony surface is flat and the colony margin is sinuous.
2 Bouillon-agar slant culture:
   Good unfolded cloth-like, orange to pale brown
3 Bouillon broth culture:
   Grows weakly in turbid suspension. No precipitation appears.
4 Bouillon gelatin stab culture:
   Grows well mainly on upper portion. Crater-like liquefaction.
5 Litmus milk : No change is observed.
(c) Physiological properties
1 Nitrate reduction: —
2 Denitrification: —
3 NM (methyl red) test : —
4 VP (Voges-Proskauer)test :
5 Indole production : —
6 Production of hydrogen sulfide(TSI agar and lead acetate paper) : —
7 Starch hydrolysis : — ~ +(weak)
8 Citrate utilization(Koser's, Christensen's and Simon's medium) : +
9 Inorganic nitrogen source utilization :
   i) Potassium nitrate : —
   ii) Ammonium sulfate : —
10 Pigment production (King's A, King's B and Mannitol yeast extract agar medium) : Production of soluble pigment of pale yellow is observed in King's B medium.
11 Urease : —
12 : Oxidase : +
13 Catalase : —
14 Temperatures for growing : 13° to 31° C., optimally 14° to 25.5° C., Medium : Bouillon liquid medium.
15 Oxygen demand : Aerobic
16 O-F (oxidative-fermentation) test [Hugh Leifson method]: Not decomposed
17 Utilization of sugar : Utilizes D-glucose, D-mannose, D-galactose, maltose, trehalose, starch and cellobiose
18 Ability of decomposing polysaccharide :
   CMC : —
   Colloidal chitin : — ~ ±
   Sodium arginate : — ~ ±
19 Hydrolysis of Tween 80 : —
20 Decarboxylation of amino acid : Ornithine : —; Arginine : —; Lysine : —.
21 GC(guanine-cytosine) content in DNA : 36.9±1.0% (Tm method)

Strain PK-176 having the afore-mentioned taxonomical characteristics was collated with bacterial species described in Bergey's Manual of Determinative Bacteriology, 8th edition, International Journal of Systematic Bacteriology, Vol.30, pp.225 to 420(1980) and ibid Vol. 32, pp.146 to 149 to find that the strain was an cream to orange-colored gram-negative rod having no flagella, showed motility by gliding and formed no spore and no microcist. Based on the following characteristics, i.e. the strain is aerobic, does not decompose high-molecular polysaccharide, and the GC content of its DNA is 36.9%, the strain was considered as bacteria belonging to the genus Flexibacter. Thus, PK-176 strain was considered as belonging to a species of the genus Flexibacter and decided to name it Flexibacter so. PK-176. Strain PK-176 is differentiated from the above-mentioned strain PK-74 in properties of nitrate reduction, inorganic nitrogen source utilization, Litmus milk, pigment production and griding ability on the skim milk plate and so on. The above-mentioned Flexibacter sp. PK-74 and PK-176 have been deposited at Fermentation Research Institute, Agency of Industrial Science and Technology, Ministry of International Trade and Industry (FRI, 1-3, Higashi-1-chome, Yatabe-gun, Ibaraki Prefecture, Japan) under the Budapest Treaty and also at the Institute for Fermentation Osaka (IFO, 2-17-85, Juso-hommachi, Yodogawa-ku, Osaka, Japan) with the accession dates and the accession numbers as shown below:

| Strain | Depositary Institution | Accession date | Accession number |
| --- | --- | --- | --- |
| PK-74 | FRI | April 2, 1988 | FERM BP-1831 |
|  | IFO | March 7, 1988 | IFO 14731 |
| PK-176 | FRI | February 20, 1989 | FERM BP-2291 |
|  | IFO | January 31, 1989 | IFO 14825 |

Bacteria belonging to the genus Flexibacter used in the present invention are, in general, readily to undergo some changes in properties, and they can be varied easily by mutations using ultraviolet ray, X-ray, chemicals (e.g. nitrosoguanidine and ethyl methanesulfonate), etc.; and strains which can be used in the present invention include all mutants capable of producing TAN-1057.

In the incubation of TAN-1057-producing bacteria, as carbon sources, the substances which can be assimilated by the bacteria, for example, glucose, fructose, maltose, soluble starch, dextrin, oils and fats (e.g. soybeam oil, olive oil, etc.), organic acids (e.g. citric acid, succinic acid, gluconic acid, etc.), etc. are used. As nitrogen sources, the organic nitrogen compounds such as soybean flour, cotton seed powder, corn gluten meal, dried yeast, yeast extract, meat extract, peptone, urea, etc. are used. Inorganic salts such as sodium chloride, potassium chloride, calcium carbonate, magnesium sulfate, potassium primary phosphate, sodium secondary phosphate, which are essential to ordinary bacterial cultures, can be adequately used singly or in combination.

Heavy metals such as ferrous sulfate and copper sulfate, and vitamins such as vitamin $B_1$ and biotin, are supplemented when required. Antifoaming agents such as silicone oil and polyalkylene glycol ether, and surface active agents, can also be added to the medium. Further, any other organic or inorganic substance which facilitate the growth of microbes and thus promote TAN-1057A production can also be added upon necessity.

As for culture methods, ordinary production methods for antibiotics can be applied; either solid or liquid culture may be applicable. In the case of liquid cultures, stationary cultures, agitating cultures, shaking culture, aeration cultures, etc. can be optimally conducted; agitating culture under aeration is especially preferable. Culture temperature is preferably in a range of about 15° C. to 32° C., preferably 15° C. to 32° C. pH is in a range of about 5 to 8, and the culture is conducted for approximately 8 to 168 hours, preferably about 24 to 144 hours. For the isolation of antibiotics TAN-1057 from cultures, separation methods which are usually used to isolate metabolites produced by microbes from their cultures can properly used. For example, TAN-1057, which is a water-soluble basic substance, is contained mainly in culture filtrate, and it is recovered advantageously by the following procedures. Namely, the whole culture broth, after addition of a filter aid, is subjected to filtration or centrifugation to remove cells. The resulting culture filtrate is brought in contact with a suitable carrier to allow active components in the filtrate to be adsorbed thereon and recover the active substances by desorbing with an appropriate solvent fractionally, and this process is counted as an advantageous one. Chromatographic carriers which can be used favorably include, among others, compounds with which adsorption power difference is applied, such as activated charcoal, powdered cellulose, and adsorptive resins, those with which functional group difference is applied, such as cation exchange resin, cation exchange cellulose, cation exchange Sephadex ®, etc. or those with which a molecular weight difference is applied, such as Sephadex ® or Bio-gel ®. Eluents which can be used in a proper combination to elute object compounds from these carriers include aqueous solutions of water-soluble organic solvents, e.g. aqueous acetone, aqueous alcohols, etc., or aqueous solutions containing acids, alkalis, buffer solutions, organic salts or inorganic salts, though combination varies with types and properties of carriers.

In some cases, crude products containing antibiotics, thus obtained chromatographically, are subjected to high performance liquid chromatography (HPLC) for separation to afford purified products. To describe it in more detail, use is made of, as the carrier, cation-exchange resin such as Amberlite IRC-50 or CG-50(manufactured by Rohm & Haas Co., USA) to allow the antibiotics in the filtrate to be adsorbed thereon, then elution is carried out using as aqueous buffer solution containing salts or acids. Further, the antibiotics can be adsorbed on a carrier for cation-exchanged gel filtration e.g. CM-Sephadex (Pharmacia Fine Chemicals, Sweden) and then thus-adsorbed material can be eluted with an aqueous or buffer solution containing salts or acids. It is recommended that activated charcoal for chromatography (manufactured by Takeda Chemical Industries, Ltd.) or adsorptive resins such as Diaion HP-20 or SP-207 (manufactured by Mitsubishi Chemical Industries, Ltd.), Amberlite XAD-II (manufactured by Rohm & Haas Co,m USA) be used removing salts and coloring substances, etc. Eluted fractions are pulverized via processes including concentration and lyophilization or crystallized from an aqueous solvent such as aqueous methanol or aqueous ethanol. When the resulting powder contains impurities, HPLC is useful for further purification. Carriers which can be used in such HPLC include TSK gel (manufactured by Toyo Soda Manufacturing Co,m Ltd.), YMC gel (manufactured by Yamamura Chemical Laboratories), etc. As the mobile phase, mixed solutions of methanol, acetonitrile or the like and an aqueous or buffer solution containing inorganic salts can be used. Incidentally, it is assumed that, in TAN-1057, different type basic groups are present, which react with a mineral acid e.g. hydrochloric acid, sulfuric acid, phosphoric acid, etc., or an organic acid e.g. formic acid, acetic acid, oxalic acid, etc. in an amount of 2 or 3 equivalents to isolate as corresponding salts. TAN-1057 salts separated thus above can be converted into free TAN-1057 by conventional means, and said free compounds can be converted to salts as mentioned above by conventional means. Physical and chemical properties of TAN-1057A trichloride, which was obtained in Example 2 to be described later are as follows.

TAN-1057A trihydrochloride (1) Appearance : Colorless solid
(2) Specific rotation : $[\alpha]_D^{20} -28 \pm 5°$ (c=1.0, in water)
(3) Molecular weight : 356(M+H)+, 394(M+K)+: (SI-MS method)

(M represents the molecular weight of free compound).

(4) Molecular formula : $C_{13}H_{25}N_9O_3 \cdot 3HCl$
(5) Elemental analysis : Samples were subjected to analysis after drying on phosphorus pentoxide at 40° C. for 6 hours. (calculated as containing 1 mole of water)(%)

| Found | Calcd. |
|---|---|
| C, 33.0 ± 2.0 | C, 32.34 |
| H, 6.0 ± 1.0 | H, 6.26 |
| N, 26.5 ± 2.0 | N, 26.11 |
| O, | O, 13.26 |
| Cl, 20.6 ± 2.0 | Cl, 22.03 |

(6) UV absorption spectrum :
$\lambda H_2O/max$ 215 $\pm 3nm(E_{1cm}^{1\%}=490 \pm 100)$ and 245$\pm 3nm(E_{1cm}^{1\%}=258\pm 50)$
$\lambda 0.1N_{max}HCl$ 205$\pm 3nm(E_{1cm}^{1\%}=710\pm 100)$
$\lambda 0.1N_{max}NaOH$ 252$\pm 3nm(E_{1cm}^{1\%}=471\pm 100)$ (7) IR absorption spectrum :
Main wave numbers are as follows: 3400, 3180, 2950, 1720, 1620, 1480, 1420, 1380, 1340, 1280, 1230, 1130, 1030, 940, 850, 670, 590(cm$^{-1}$)

$13_C$ NMR spectrum :
The following signals are measured in deuterium oxide at 75MHz, γ ppm: 175.2(s), 171.9(s), 159.5(s), 158.5(s), 156.3(s), 56,8(d), 50.9(d), 43.2(t), 41.3(t), 37.6(q), 37.5(t), 31.9(t), 26.7(t)
(s : singlet, d : doublet, t : triplet, q : quartet)

(9) HPLC :
Column : YMC-PAK A312 (Yamamura Chemical Laboratories)
Mobile phase: 0.01M phosphoric acid solution (pH 3)
Flow rate : 2ml/min. Rt =3.8(minutes)

(10) Color reaction :
Positive : Dragendorff's, Sakaguchi's, Greig-Leaback's reaction
Negative: Ehrlich's reaction

(11) Solubility :
Readily soluble ; water
Soluble ; dimethylsulfoxide, methanol
Sparingly soluble ; acetone, ethyl acetate, diethyl ether

(12) Acidity or basicity : neutral (Free compound is basic)

And, physical and chemical properties of TAN-1057A dihydrochloride, which was obtained in Example 3 to be described later.

TAN-1057A dihydrochloride (1) Appearance : Colorless solid
(2) Specific rotation : $[\alpha]_D^{23} -34°$ $\pm 5°$ (c=1.0, in water) Molecular weight : 356(M+H)+, 394(M+K)+; (SI-MS method.
(4) Molecular formula : $C_{13}H_{25}N_9O_3 \cdot 2HCl$
(5) Elemental analysis : Samples were subjected to analysis after drying on phosphorus pentoxide at 40° C. for 6 hours under reduced pressure. (calculated as containing 1 mole of water)(%)

| Found | Calcd. |
|---|---|
| C, 34.1 ± 2.0 | C, 34.98 |
| H, 6.7 ± 1.0 | H, 6.55 |
| N, 27.6 ± 2.0 | N, 28.24 |
| O, | O, 14.34 |
| Cl, 16.2 ± 2.0 | Cl, 15.89 |

(6) UV spectrum : cf. FIG. 1
$\lambda H_{max}^2O$ 215$\pm 3nm(E^{1\%}=524\pm 100)$, 245 3nm$(E_{1cm}^{1\%}=269\pm 50)$ (7) IR spectrum : cf. FIG. 2 Main wave numbers are as follows : 3400, 3180, 2950, 1720, 1620, 1480, 1420, 1380, 1340, 1280, 1230, 1130, 1030, 940, 850, 670, 590(cm$^{-1}$)

(8) $^{13}$C NMR spectrum :
The following signals are measured in deuterium oxide at 75MHz, γ ppm: 178.6(s), 175.3(s), 161.9(s), 160.6(s), 159.7(s), 56.4(d), 51.2(d), 43.5(t), 41.4(t), 37.8(t), 36.9(q), 32.1(t), 27.0(t).

(9) HPLC :
Column : YMC-PAK A 312
Mobile Phase : 0.01M phosphoric acid solution (pH 3),
Flow rate : 2 ml /min.
Rt : 3.8 (minutes)

(10) Color reaction :
Positive : Dragendorff's, Sakaguchi's, GreigLeaback's reactions
Negative : Ehrlich's reaction

(11) Solubility :
Readily soluble : water
Soluble : dimethyl sulfoxide, methanol
Sparingly soluble : acetone, ethyl acetate, diethyl ether

(12) Acidity or basicity : neutral (Free compound is basic.)

(13) Structural formula:

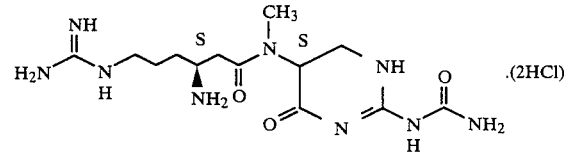

Physical and chemical properties of TAN-1057B dihydrochloride, which was obtained in Example 4 to be described later are as follows.

TAN-1057B dihydrochloride (1) Appearance : Colorless solid
(2) Specific rotation : $[\alpha]_D^{22} +73\pm 10°$ (c=1.0, in water)
(3) Molecular weight : 356(M+H)+(SI-MS method)
(4) Molecular formula : $C_{13}H_{25}N_9O_3 \cdot 2HCl$
(5) Elemental analysis :
Samples were subjected to analysis after drying on phosphorus pentoxide at 40° C. for 6 hours.
(calculated as containing 1.5 mole of water)(%)

| Found | Calcd. |
|---|---|
| C, 34.2 ± 2.0 | C, 34.29 |
| H, 6.7 ± 1.0 | H, 6.64 |

-continued

| Found | Calcd. |
|---|---|
| N, 27.6 ± 2.0 | N, 27.68 |
| O, | O, 15.81 |
| Cl, 16.7 ± 2.0 | Cl, 15.57 |

(6) UV absorption spectrum : cf. FIG. 3
$\lambda max/H_2O$ 215±3nm($E_{1cm}^{1\%}$=510±100) and 245±3nm($E_{1cm}^{1\%}$=260±50)
$\lambda 0.1_{max}^{N\ HCl}$205±3nm($E_{1cm}^{1\%}$=705±100)
$\lambda 0.1_{max}^{N\ NaOH}$252±3nm($E_{1cm}^{1\%}$451±100)

(7) IR spectrum : cf. FIG. 4
Main wave numbers are as follows: 3400, 3180, 2950, 1720, 1620, 1480, 1380, 1340, 1280, 1130, 1030, 940, 850, 770, 670, 650, 590(cm.$^{-1}$) p1 (8) 13C NMR spectrum :
The following signals are measured in deuterium oxide at 75MHz, γ ppm: 178.5(s), 175.3(s), 161.8(s), 160.6(s), 159.7(s), 56.6(d), 51.2(d), 43.5(t), 41.5(t), 37.7(t), 37.2(t), 32.1(t), 27.0(t)

(9) HPLC :
Column : YMC-PAK A312
Mobile phase: 0.1M phosphoric buffer (pH 5)
Flow rate 2ml/min. Rt =5.3 (minutes) (when Rt of TAN-1057A is 5.7 minutes)

(10) Coloration reaction :
Positive : Dragendorff's, Sakaguchi's, GreigLeaback's reaction
Negative Ehrlich's reaction

(11) Solubility :
Readily soluble ; water
Soluble ; dimethylsulfoxide, methanol
Sparingly soluble ; acetone, ethyl acetate, diethyl ether

(12) Acidity or basicity : neutral (Free compound is basic)

(13) Structural formula :

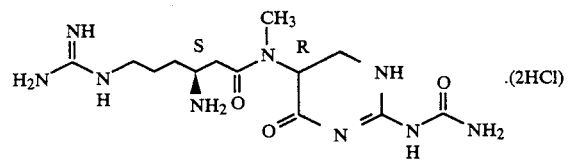

And, physical and chemical properties of TAN-1057 dihydrochloride, which was obtained in Example 6 to be described later.

TAN-1057C dihydrochloride (1) Appearance : Colorless solid
(2) Specific rotation $[\alpha]_D^{23} -40 \pm 5°$ (c=0.5, in water)
(3) Molecular weight : 356(M+H)+(SI-MS method)
(4) Molecular formula : $C_{13}H_{25}N_9O_3.2HCl$
(5) Elemental analysis : Samples were subjected to analysis after drying on phosphorus pentoxide at 40° C. for 6 hours under reduced pressure. (calculated as containing 2.5 mole of water)(%)

| Found | Calcd. |
|---|---|
| C, 33.1 ± 2.0 | C, 32.99 |
| H, 6.5 ± 1.0 | H, 6.81 |
| N, 26.2 ± 2.0 | N, 26.63 |
| O, | O, 18.59 |
| Cl, 16.8 ± 2.0 | Cl, 14.98 |

(6) UV absorption spectrum :
The end absorption only is observed in water or 0.1N HCl
$\lambda 0.1N\ _{max}^{NaOH}$ 221±3nm($E_{1cm}^{1\%}$=295±100), 252±3nm($E_{1cm}^{1\%}$=333±100)

(7) IR spectrum : cf. FIG. 5
Main wave numbers are as follows: 3380, 3180, 2950, 1730, 1640, 1470, 1400, 1340, 1250, 1210, 1160, 1100, 980, 600(cm$^{-1}$)

(8) $^{13}$C NMR spectrum :
The following signals are measured in deuterium oxide at 75MHz, γ ppm1: 176.6(s), 173.0(s), 159.7(s), 158.7(s), 157.2(s), 65.4(d), 52.7(d), 45.3(t), 43.6(t), 41.5 (t), 35.0(t), 27.4(t)

(9) Circular dichlorium (CD)spectrum in water $[\theta]_{232}^{26.5} +13,700$

(10) HPLC :
Column : YMC-PAK A 312
Mobile Phase : 0.1M phosphoric acid solution (pH 5),
Flow rate : 2 ml /min.
Rt : 15.5 (minutes) (when Rt of TAN-1057 A is 5.7 minutes.)

(11) Color reaction :
Positive : Dragendorff's, Sakaguchi's, GreigLeaback's reactions
Negative : Ehrlich's reaction

(12) Solubility :
Readily soluble : water
Soluble : dimethyl sulfoxide, methanol
Sparingly soluble : acetone, ethyl acetate, diethyl ether

(13) Acidity or basicity : neutral (Free compound is basic.)

(14) Structural formula:

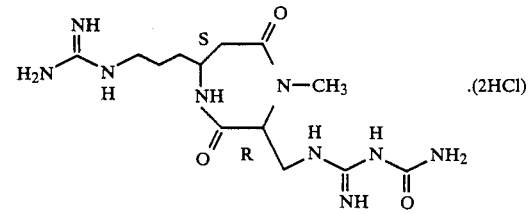

Physical and chemical properties of TAN-1057D dihydrochloride, which was obtained in Example 6 to be described later are as follows.

TAN-1057D dihydrochloride (1) Appearance : Colorless solid
(2) CD spectrum : $[\theta]_{233}^{24}$- 10,500, (in water)
(3) Molecular weight : 356(M+H)+, (SI-MS method)
(4) Molecular formula : $C_{13}H_{25}N_9O_3.2HCl$
(5) Elemental analysis :
Samples were subjected to analysis after drying on phosphorus pentoxide at 40° C. for 6 hours. (calculated as containing 3.5 mole of water)(%)

| Found | Calcd. |
|---|---|
| C, 32.0 ± 2.0 | C, 31.78 |
| H, 6.4 ± 1.0 | H, 6.97 |
| N, 25.4 ± 2.0 | N, 25.65 |
| O, | O, 21.16 |
| Cl, 15.3 ± 2.0 | Cl, 14.43 |

(6) UV spectrum :

The end absorption only is observed in water or 0.1N HCl.

$\lambda 0.1_{max}^{N\ NaOH} 24\pm 3nm(E_{1cm}^{1\%}=348\pm 100)$ and $252\pm 3nm(E_{1cm}^{1\%}=141\pm 50)$ (7) IR spectrum : cf. FIG. 6

Main absorption wavenumbers are as follows: 3380, 3190, 2950, 1730, 1650, 1470, 1420, 1340, 1250, 1170, 1110, 980, 600(cm$^{-1}$)

(8) $^{13}$C NMR spectrum :

The following signals are measured in deuterium oxide at 75MHz, $\gamma$ ppm: 177.2(s), 173.2(s), 159.7(s), 158.7(s), 157.2(s), 63.2(d), 53.1(d), 44.3(t), 43.6(t), 41.6(t), 36.1(g), 35.6(t), 26.7 (t)

(9) HPLC :

Column : YMC-PAK A312

Mobile phase: 0.1M phosphoic acid solution (pH 5)

Flow rate 2ml/min. Rt =16.7 (minutes) (when Rt of TAN-1057A is 5.7 minutes)

(10) Color reaction :

3 Positive : Dragendorff's, Sakaguchi's, GreigLeaback's reaction

Negative: Ehrlich's reaction

(11) Solubility :

Readily soluble ; water

Soluble ; dimethylsulfoxide, methanol

Sparingly soluble ; acetone, ethyl acetate, diethyl ether

(12) Acidity or basicity : neutral (Free compound is basic)

(13) Structural formula :

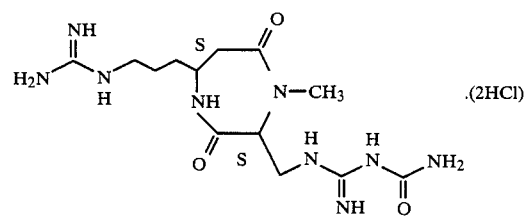

As explained above, TAN-1057A, B, C and D have the same molecular formula, and the relations among them are shown below:

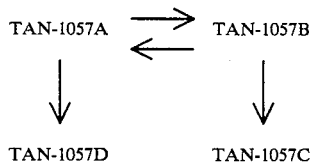

Namely, TAN-1057A and B are converted easily each other in aqueous solution at room temperature, A to B and B to A, to give a mixture thereof in a constant ratio. For example, in case that the mixture of TAN-1057A and B is isolated as crystals of the sulfate, the ratio of TAN-1057A and B is about 6 to 8:4 to 2.

On the other hand, it was confirmed by HPLC that each TAN-1057C and D is converted into TAN-1057B and TAN-1057A, respectively, in an aqueous solution, especially in aqueous alkaline solution. As an example, Example 8 shows that TAN-1057C is converted into TAN-1057B ( to give a mixture of TAN-1057A and B as a result). The term "Antibiotics TAN-1057" in the present specification includes also a mixture which contains TAN-1057A, B, C and D in an optional combination and an optional ratio thereof.

The biological activities of TAN-1057 are described as follows. The antibacterial activities of TAN-1057A against various bacteria are as shown in Table 1.

TABLE 1

| Test Organisms | Minimum Inhibitory Conc. (MIC, μg/ml) (Note 1) | | |
|---|---|---|---|
| | pH 5 | pH 7 | pH 9 |
| *Staphylococcus aureus* FDA 209P | NG | 3.13 | <0.1 |
| *Staphylococcus epidermidis* IFO 3762 | >100 | 1.56 | <0.1 |
| *Micrococcus luteus* IFO 12708 | NG | 1.56 | 0.2 |
| *Bacillus subtilis* NIHJ PCI 219 | 50 | 12.5 | 1.56 |
| *Bacillus cereus* FDA 5 | 6.25 | 25 | 3.13 |
| *Bacillus megaterium* IFO 12108 | 25 | 12.5 | 1.56 |
| *Streptococcus faecalis* IFO 3989 | >100 | 12.5 | 3.13 |
| *Escherichia coli* NIHJ JC 2 | >100 | >100 | 25 |
| *Escherichia coli* LD-2 | 100 | 25 | 1.56 |
| *Salmonella typhimurium* IFO 12529 | >100 | >100 | 25 |
| *Klebsiella pnemoniae* IFO 3317 | >100 | >100 | 100 |
| *Proteus vulgaris* IFO 3988 | >100 | >100 | 50 |
| *Pseudomonas aeruginosa* IFO 3080 | >100 | >100 | 100 |
| *Pseudomonas aeruginosa* PAO-8 | 100 | >100 | 100 |
| *Aeromonas caviae* NCW | 100 | 6.25 | 1.56 |
| *Acinetobacter calcoaceticus* IFO 13006 | 1.56 | 6.25 | 1.56 |
| *Acinetobacter calcoaceticus* IFO 12552 | 12.5 | 6.25 | 1.56 |

(Note 1) Measurement was conducted by employing a medium consisting of Bacto Antibiotic Medium 3 (Difco Laboratories, USA)(17.5 g), Bacto yeast extract(Difco Laboratories, USA)(5.0 g) and distilled water(pH designated)(1000 ml), using approximately 10$^5$ colony forming unit/ml of inoculum, by means of the broth dilution method.
(Note 2) NG: No growth Antibacterial activity of TAN-1057 A against *Staphylococcus aureus* clinically isolated is shown in the following table 2.

TABLE 2

| Strain | MIC(μg/ml) | | | | |
|---|---|---|---|---|---|
| | TAN-1057A | DMPPC | KM | GM | EM |
| FDA 209P | 0.39 | 1.56 | 0.39 | ≦0.20 | 0.39 |
| N8 | 0.78 | 1.56 | 1.56 | ≦0.20 | >100 |
| N91 | 0.78 | 1.56 | >100 | 0.39 | 0.39 |
| N51 | 0.78 | 1.56 | 3.13 | 0.39 | 0.39 |
| N235 | 1.56 | 1.56 | 100 | >100 | >100 |
| N62 | 0.78 | 3.13 | 25 | 3.13 | >100 |
| N83 | 0.39 | 3.13 | >100 | ≦0.20 | >100 |
| N176 | 1.56 | 12.5 | 3.13 | 0.39 | >100 |
| C3 | 0.78 | 50 | >100 | 100 | >100 |
| C4 | 6.25 | 50 | >100 | 50 | 0.39 |
| N247 | 1.56 | 50 | >100 | 50 | 6.25 |
| N129 | 0.39 | 400 | >100 | 50 | 0.39 |
| N267 | ≦0.20 | 100 | >100 | 100 | >100 |
| N237 | 0.78 | 20 | >100 | >100 | >100 |
| N262 | 0.78 | 100 | >100 | 50 | >100 |
| N121 | 0.78 | 50 | >100 | >100 | 0.39 |
| N28 | 0.78 | 1600 | >100 | 0.39 | >100 |
| C7 | 0.78 | 50 | >100 | >100 | 12.5 |
| C10 | 0.78 | 800 | >100 | >100 | >100 |
| N64 | 0.78 | 1600 | >100 | 0.78 | >100 |
| N326 | 0.78 | 1600 | >100 | >100 | >100 |
| TS-65 | 0.78 | >1600 | >100 | 100 | >100 |
| TST-75 | 0.78 | 12.5 | >100 | >100 | >100 |
| N176-3 | 1.56 | 50 | 1.56 | 0.39 | >100 |
| N176-6 | 0.78 | 200 | 1.56 | 0.39 | >100 |
| N247-16 | 0.78 | >1600 | >100 | 100 | 3.13 |
| N247-21 | 0.78 | 200 | >100 | 50 | 6.25 |

DMPPC: Methicillin, KM: Kanamycin, GM: Gentamycin, EM: Erythromycin
(Note) Determined by the agar dilution method. Medium: Mueller Hinton medium (Difco, USA) Inoculum Size: 10$^6$ CFU/ml, 37° C.

TAN-1057A is further effective against anaerobic bacteria, Spirochaeta and Mycoplasma, etc., as shown in Table 3.

TABLE 3

| Test Organism | MIC(μg/ml) |
|---|---|
| Anaerobic bacteria[Note 1] | |
| Peptostreptococcus anaerobium B-40 | 25 |
| Eubacterium sp. biurens 515 | 12.5 |
| Bacteroides thermophilis PNA-1-24 | 0.78 |
| Lactobacillus acidophilus ATCC 4356 | 6.25 |
| Bacteroides fladilis ATCC 2509 | 50 |
| Fusobacterium necroform VPI 2891 | 3.13 |
| Clostridium perfringens PB6K | 12.5 |
| Spirochaeta[Note 2] | |
| Treponema hyodicenterie DJ70PI | 100 |
| Treponema hyodicenterie 78/A | 100 |
| Mycoplasma[Note 3] | |
| Mycoplasma garisepticum S6 | 3.13 |
| Mycoplasma garisepticum TB-3A | 3.13 |
| Mycoplasma pulmonis M-53 | 0.39 |

Inoculum size: $10^6$ CFU/ml
[Note 1] GAM medium(Nissui), Gas Pack (BBL), 37° C., 18 hours
[Note 2] 20% Horse serum/TSA medium, Gas Pack (BBL), 37° C., 48 hours
[Note 3] Hayflick medium, 37° C., 5 days

TABLE 4

| | Minimum Inhibitory Conc. (MIC, μg/ml) (Note 1) TAN-1057 | | | |
|---|---|---|---|---|
| Test Organisms | A | B | C | D |
| Staphylococcus aureus FDA 209P | 6.25 | 25 | 50 | 6.25 |
| Staphylococcus epidermidis IFO 3762 | 0.78 | 3.13 | 6.25 | 0.78 |
| Micrococcus luteus IFO 12708 | 3.13 | 12.5 | 12.5 | 3.13 |
| Bacillus subtilis NIHJ PCI 219 | 12.5 | 50 | >100 | 12.5 |
| Bacillus cereus FDA 5 | 25 | 100 | >100 | 25 |
| Bacillus megaterium IFO 12108 | 12.5 | 50 | >100 | 12.5 |
| Streptococcus faecalis IFO 3989 | 12.5 | 50 | 50 | 12.5 |
| Escherichia coli NIHJ JC 2 | >100 | >100 | >100 | >100 |
| Escherichia coli LD-2 | 12.5 | 25 | 50 | 12.5 |
| Salmonella typhimurium IFO 12529 | 100 | >100 | >100 | >100 |
| Klebsiella pnemoniae IFO 3317 | >100 | >100 | >100 | >100 |
| Proteus vulgaris IFO 3988 | >100 | >100 | >100 | >100 |
| Pseudomonas aeruginosa IFO 3080 | >100 | >100 | >100 | >100 |
| Pseudomonas aeruginosa C141V | 6.25 | 25 | 50 | 1.25 |
| Aeromonas caviae NCW | 12.5 | 25 | 50 | 6.25 |
| Acinetobacter calcoaceticus IFO 12552 | 50 | 100 | >100 | 25 |

(Note 1) Measurement was conducted by employing a medium consisting of DYA medium [Bacto Antibiotic Medium 3 (Difco Laboratories, USA)(17.5 g), Bacto yeast extract(Difco Laboratories, USA)(5.0 g) and distilled water(pH unadjusted)(1000 ml)], using approximately $10^6$ colony forming unit/ml of inoculum, by means of the agar dilution method.

The therapeutic effects of TAN-1057A to infectious diseases in mice are as shown in Table 5.

TABLE 5

| Infectious Disease[Note 1] | Administration Route | $ED_{50}$ (mg/kg) |
|---|---|---|
| Staphylococcus aureus 308A-1 | Subcutaneous | ca. 0.1 |
| Staphylococcus aureus 308A-1 | Oral | ca. 1.0 |

[Note 1] ip infection

Further, TAN-1057 is effective to experimental cells of malignant tumor such as lymph nodes tumor P 388, recticulum cell sarcoma M5076 in vivo test. Table 6 shows the results obtained by intraperitoneal injection of. TAN-1057A and B (mixture) to tumor bearing mice obtained by inoculating P 388 according to intraperitoneal injection.

TABLE 6

| Dose (time) | Prolongation effect of life span (T/C, %) |
|---|---|
| 10 mg/kg (4) | 176 |
| No treatment | 100 |

Further, the acute toxicity of TAN-1057A in mice is as shown in Table 7.

TABLE 7

| Route | $LD_{50}$(mg/kg) |
|---|---|
| Intraperitoneal | Approx. 100 |
| Oral | >400 |

As clearly shown in these data, TAN-1057 and its salts have strong antibacterial activity against, for example, both gram-positive and gram-negative bacteria, spirochaeta and mycoplasma and have strong growth inhibition against tumor cells, while showing low toxicity in mammals. Moreover, TAN-1057 and its salts are effective to various types of drug-resistant bacteria and do not show cross resistance. Therefore, TAN-1057 and their salts can be widely used in the therapeutics of infectious diseases caused by pathogenic microorganisms or tumors in mammals (e.g. mice, rats, rabbits, chickens, pigs, cows, dogs, humans)

For using TAN-1057 or their salts as therapeutic drugs of, for example, infectious diseases, they are mixed with pharmacologically acceptable carriers, excipients, diluents, etc., and are administered as, for example, injecitons parenterally to the above-mentioned mammals subcutaneously, intravenously or intramuscularly at a dose of about 0.01 to 10 mg/kg/day, preferably about 0.02 to 5 mg/kg/day. For example, for using TAN-1057A or its salts, they are prepared into capsules or tablets and administered at a dose of about 0.1 to 50 mg/kg/day, preferably about 0.2 to 25 mg/kg/day.

Besides, TAN-1057A, an equilibrium mixture of TAN-1057A and B or its salts can be used as bactericides. For example, hands, legs, eyes, ears, etc. can be sterilized and disinfected by applying TAN-1057A or its salts on these portions as a liquid prepared by dissolving them in distilled water at a concentration of approx. 0.001 to 0.1 w/v % or as an ointment containing approx. 0.01 to 1 mg, preferably approx. 0.02 to 0.5 mg in terms of TAN-1057A per gram.

TAN-1057s of the present invention are novel antibiotic substances produced by bacteria, and strongly inhibits the growth of pathogenic microorganisms and malignant tumors, thus being useful as therapeutic agents of, for example, infectious diseases or antitumor agents as clinically applicable pharmaceuticals or animal drugs.

BRIEF EXPLANATION OF DRAWINGS

FIG. 5 and FIG. 6 respectively show each IR spectrum of TAN-1057C dihydrochloride and TAN-1057D dihydrochloride.

Figure 1:
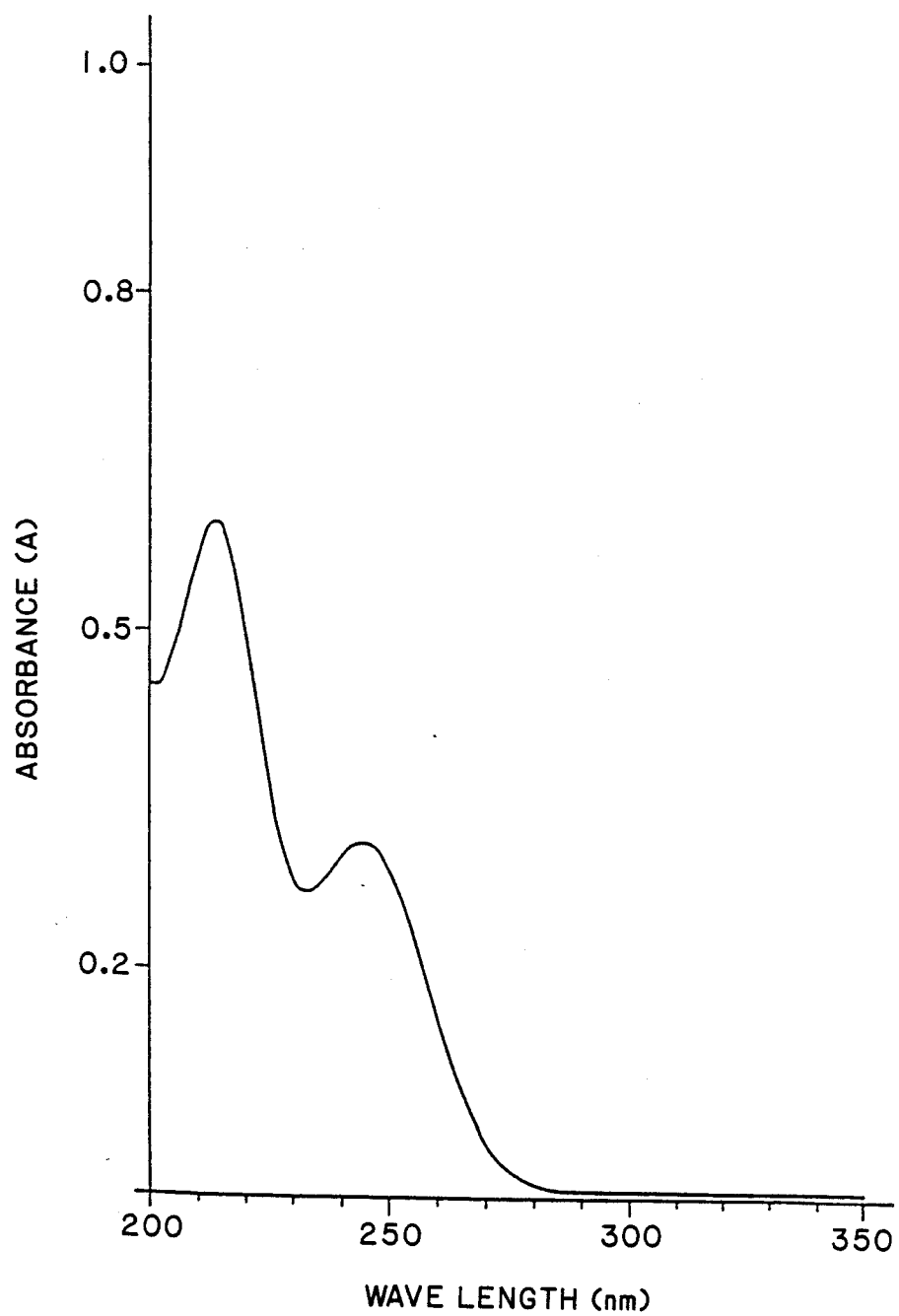
FIG. 1 and FIG. 2 respectively show UV and IR spectrum of the antibiotic TAN-1057A dihydrochloride.
Figure 2:
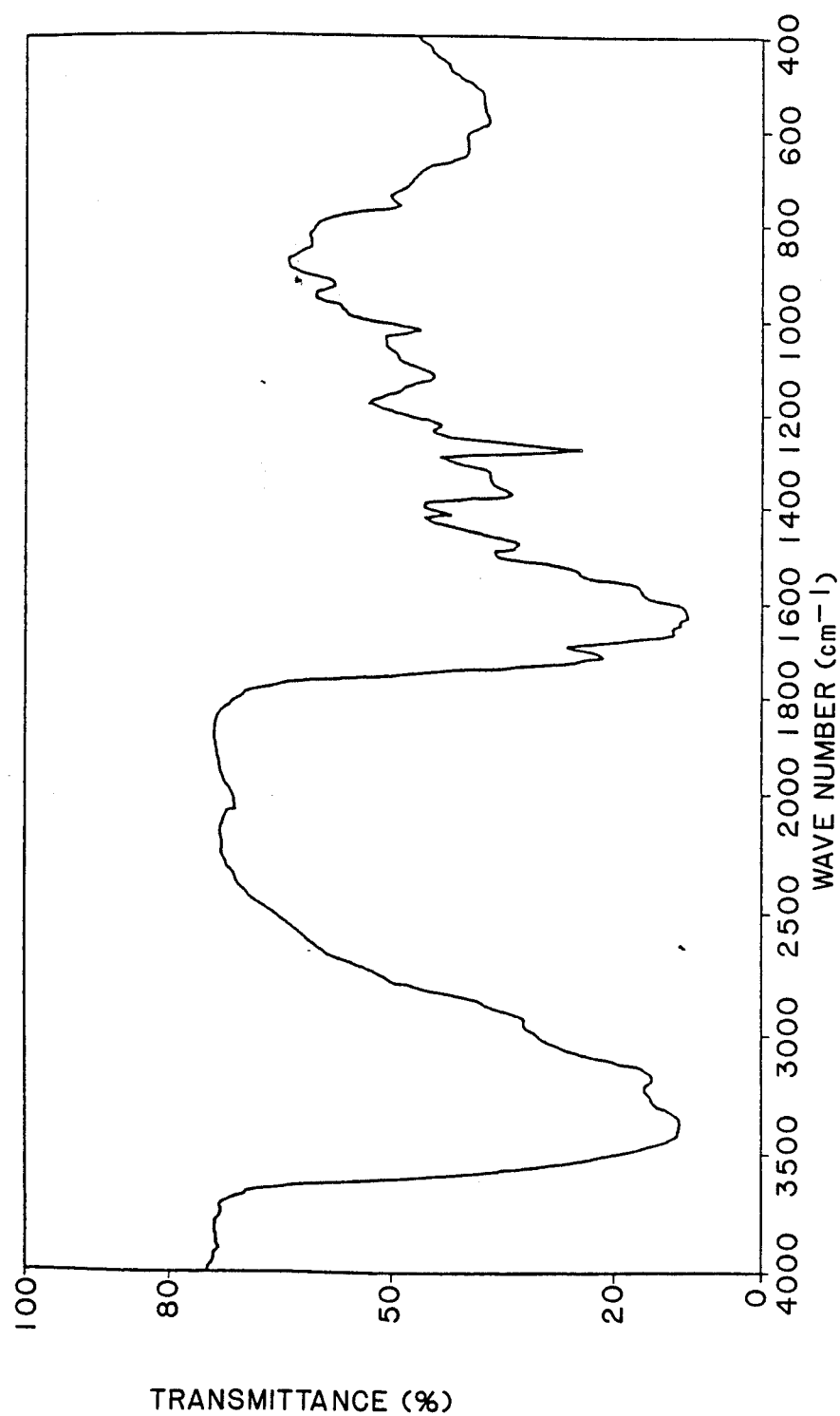
Figure 3:
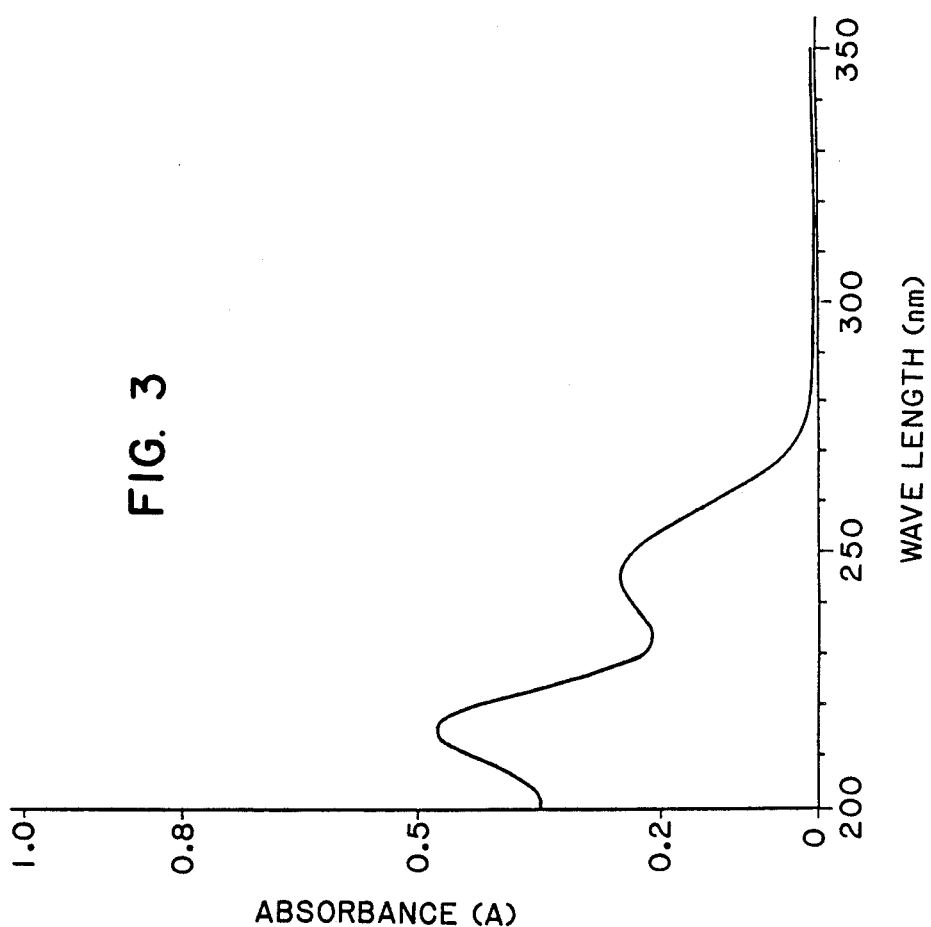
FIG. 3 and FIG. 4 respectively show UV and IR spectrum of TAN-1057B dihydrochloride.
Figure 4:
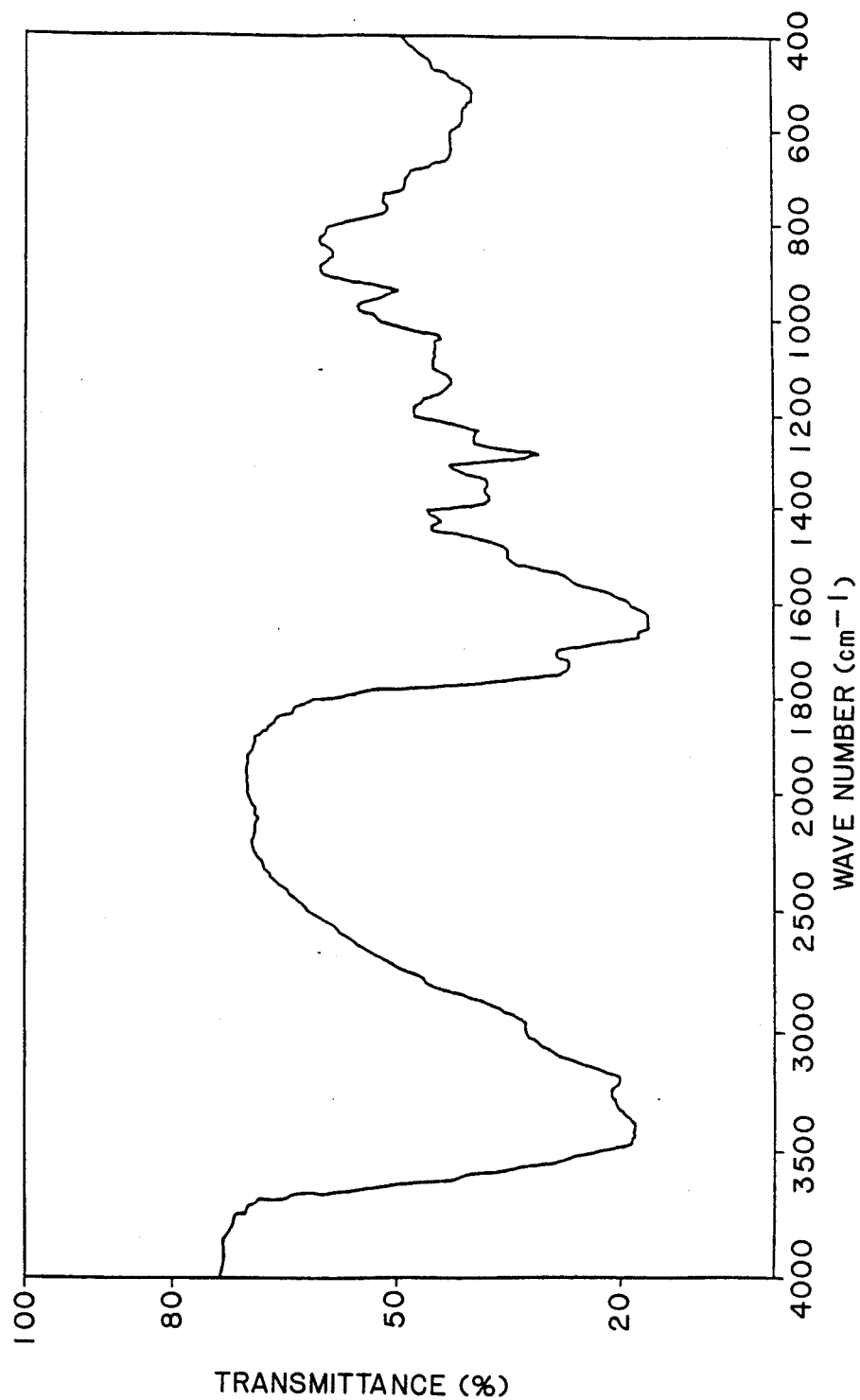

The present invention is hereinafter described in more detail by way of examples. Percentages used in the medium composition contents are weight/volume % unless otherwise specified.

EXAMPLE 1

Flexibacter sp. PK-74 (FERM BP-1831; IFO 14731) grown on a nutrient agar slant medium was inoculated into a 2000 ml Sakaguchi flask containing 500 ml of a medium prepared by adding 0.5% precipitating calcium carbonate to an aqueous solution (pH 7.0) containing 2% glucose, 3% soluble starch, 1% unprocessed soybean flour, 0.3% corn steep liquor, 0.5% Polypepton (manufactured by Nihon Pharmaceutical Co., Ltd.) and 0.3% sodium chloride, which was subjected to shaking culture at 24° C. for 48 hours. With 500 ml of the seed culture obtained above was inoculated 30l of a medium prepared by adding 0.05% Actcol (an antifoaming agent, manufactured by Takeda Chemical Industries, Ltd.) contained in a 50l fermentor. Cultivation was carried out at 24° C. under aeration of 30l/min and agitation at 200 rpm for 48 hours. With 6l of the resulting culture broth was inoculated 120l of a medium comprising 3.0% dextrin, 1.5% unprocessed soybean flour, 1.5% corn gluten meals, 0.2% Polypepton, 0.1% sodium thiosulfate, 0.5% precipitating calcium carbonate and 0.05% Actcol (pH unadjusted) in a 200l fermentor. Cultivation was carried out at 17° C. under aeration of 120l min and agitation at 170 rpm for 66 hours.

EXAMPLE 2

To 110l of the culture broth obtained in Example 1 was added Hyflo Super-Cel (manufactured by Johnes-Manville Product, U.S.A.), and the mixture was filtered to give filtrate (85l) The filtrate adjusted to pH 7.0 was applied to a column of IRC-50 (Na+ $^{type}$, 2.5l), eluting with 0.2N hydrochloric acid (25l). The eluate adjusted to pH 7.0 was chromatographed on activated charcoal (1.5l), eluting with 8% aqueous isobutanol (7.5l). The eluate was concentrated and lyophilized to give a crude powder (9.9 g). This crude powder (9.8 g) in water was subjected to a column of CM Sephadex C-25 (Na+-type, 0.25l), eluting with 0.2M saline solution (4.5l).

The desalted solution by activated charcoal chromatography (0.2l) was concentrated and lyophilized to give a powdery product mainly containing TAN-1057A (4.1 g).

This powdery product (4.1 g) was subjected to a preparative reversed-phase HPLC [column : YMC PAK R-355 (manufactured by Yamamura Chemical Laboratories), mobile phase : 0.01M phosphate buffer (pH 6.3)]to give active fractions. The fractions desalted by an activated charcoal chromatography (0.5 l) was passed through a column of IRA-402 (Cl-type) (25 ml). The effluent was concentrated and lyophilized to give TAN-1057A trihydrochloride as white powder (0.90 g).

EXAMPLE 3

Bioactive fractions obtained by similar process onto the step of a preparative HPLC in Example 2 (sample used : 6 g) were passed through a column of IRA-402 (Cl-type, 100 ml). The effluent was subjected to an activated charcoal chromatography (150 ml) and the active fractions were eluted with 8% aqueous isobutanol. The eluate was concentrated and lyophilized to afford TAN-1057A dihydrochloride (1.56 g) as white powder.

EXAMPLE 4

The powdery mixture (700 mg) containing TAN-1057A and B (the ratio of A:B is about 60:40), which was obtained at the same time on the preparative HPLC in Example 2, was subjected to a preparative HPLC [column : YMC-PAK ODS-5 (manufactured by Yamamura Chemical Laboratories), mobile phase:0.1M phosphate buffer (pH 5.0)]to give active fractions. These fractions were desalted by activated charcoal chromatography (45 ml), concentrated and lyophilized to give the mixture of TAN-1057A and B (A:B is about 40:60) as powder (491 mg).

The powder (491 mg) was again subjected to the prep-HPLC mentioned above to give a mixture of TAN-1057A and B (A:B is about 30:70) as powder (200 mg).

The powder (38 mg) was further subjected to the prep-HPLC mentioned above to give active fractions. These active fractions was passed through a column of IRA-402 (Cl-type, 10 ml). The effluent was chromatographed on an activated charcoal (2 ml), eluting 8% aqueous isobutanol. The eluate was concentrated and lyophilized to give TAN-1057B.2HCl as white powder (5 mg).

EXAMPLE 5

Flexibacter sc. PK-176 (FERM BP-2291; IFO 14825) grown on a nutrient agar slant medium was inoculated into a 2000 ml Sakaguchi flask containing 500 ml of a medium prepared by adding 0.5% precipitating calcium carbonate to an aqueous solution (pH 7.0) containing 2% glucose, 3% soluble starch, 1% unprocessed soybean flour, 0.3% corn steep liquor, 0.5% Polypepton and 0.3% sodium chloride, which was subjected to shaking culture at 24° C. for 48 hours. With 500 ml of the seed culture obtained above was inoculated 30l of a medium prepared by adding 0.05% Actcol contained in a 50l fermentor. Cultivation was carried out at 24° C. under aeration of 30l/min and agitation at 200 rpm for 48 hours. With 6l of the resulting culture broth was inoculated 120l of a medium comprising 1.5% unprocessed soybean flour, 1.5% corn gluten meals, 0.2% Polypepton, 0.5% precipitating calcium carbonate and 0.05% Actcol (pH 6.0) in a 200l fermentor. Cultivation was carried out at 17° C. for 66 hours under aeration of 120l /min and agitation at 120 rpm.

EXAMPLE 6

To 110l of the culture broth obtained in Example 5 was added Hyflo Super-Cel and the mixture was filtered to give a filtrate (100l). The filtrate adjusted to pH 5.6 was applied to a column of IRC-50 (Na+type, 2.5l), eluting with 0.2N hydrochloric acid (25l). The eluate adjusted to pH 5.5 was applied to a column of activated charcoal (1.0l), and the bioactive fractions were eluted with 8% aqueous isobutanol (7.5l). The eluate was concentrated and lyophilized to give a crude powder (3.3 g). The crude powder (8.0 g) thus obtained in water was subjected to pass through a column of CG-50 (Na+-type, 150ml). The active fractions were eluted with 0.4M saline solution (750ml) and then with 1M saline solution (900 ml). The bioactive elutions of 0.4M saline was desalted by activated charcoal chromatography. The eluate desalted was concentrated and lyophilized to give a powder (1.2 g) containing TAN-1057C and D.

The powder (1.2 g) in water was chromatographed on a column of CM-Sephadex C-25 (Na+type, 50 ml), eluting with 0.1M saline (500 ml) and 0.2M saline (750 ml).

The eluate of 0.2M saline in a volume of 9 to 14 times as much as the carrier used was desalted by activated charcoal chromatography (25 ml).

The eluate was concentrated and lyophilized to give a powder (343 mg) containing TAN-1057C and D.

The powder (300 mg) was loaded to a prep. HPLC [column: YMC-PAK ODS-5, mobile phase: 0.01M phosphate buffer (pH 5.0)]to give two bioactive components. The fractions showing the former peak was passed through a column of IRA-402 (Cl- type, 10 ml) and the effluent was desalted by active charcoal chromatography (15 ml). The eluate was concentrated, lyophilized and pulverized with acetone to give TAN-1057C.2HCl (95 mg). Similarly, the fractions showing the latter peak was passed through IRA-402 (Cl-type, 15 ml) and the effluent was desalted by active charcoal chromatography (6 ml). The eluate was concentrated, lyophilized and pulverized with acetone to give TAN-1057D.2HCl (23 mg).

EXAMPLE 7

Flexibacter sp. PK-74 (FERM BP-1831; IFO 14731) grown on a nutrient agar slant medium was inoculated into two of a 2 l Sakaguchi flask containing 500 ml of a medium prepared by adding 0.5% precipitating calcium carbonate to an aqueous solution (pH 7.0) containing 2% glucose, 3% soluble starch, 1% unprocessed soybean flour, 0.3% corn steep liquor, 0.5% Polypepton and 0.3% sodium chloride, which was subjected to reciprocating shaken culture at 24° C. for 48 hours. With the whole amount of the seed culture obtained above was inoculated 120 l of an above mentioned medium prepared by adding 0.05% Actcol contained in a 2000 l fermentor. Cultivation was carried out at 24° C. for 48 hours under aeration of 200l/min and agitation at 150 rpm. With 100 l of the resulting culture broth was inoculated 3600 l of a medium prepared by adding 0.05% Actcol to a solution (pH 6.5) containing 1.5% glucose, 3% dextrin, 2% defatted soyflour and 0.25% sodium thiosulfate in a 6000 l fermentor. Cultivation was carried out at 17° C. for 42 hours under aeration of 3600 l/min and agitation at 80 rpm.

The pH of the culture broth obtained above was adjusted to 7.0, then to the culture broth was added Hyflo Super-Cel, and the mixture was filtered. The filtrate adjusted to pH 7.0 (3750 l), was applied to a column of Cepa beads SP-207 (150 l, manufactured by Mitsubishi Chemicals). The bioactive compound was eluted with N/150 hydrochloric acid (2000 l). The eluate was subjected to a column chromatography of IRC-50 (Na+type, 100 l), eluting with 0.3NHCl (1000 l). The eluate was applied to active charcoal chromatography (50 l), eluting with 8% isobutanol N/200 HCl. The eluate was concentrated to 10 l and the concentrate was applied to a column of CG-50 (Na+type, 2 l), eluting with 0.2M sodium sulfate (10 l) and then 0.5M sodium sulfate (20 l). The active fractions, eluted with 0.5M sodium sulfate in a volume of 3 to 9 times as much as the carrier used, was desalted with active charcoal chromatography (1.5 l), eluting with 8% aqueous isobutanol (6l). The eluate was concentrated to 500 ml after addition of methanol (50 ml) and allowed to stand at 4° C. White needles thus obtained were a mixture of TAN-1057A and B sulfate (55.5 g). From HPLC analysis data, the ratio of TAN-1057A and B in these crystals was 81:19.

EXAMPLE 8

| Capsule | |
|---|---|
| (1) TAN-1057A and B (equilibrium mixture) | 50 mg |
| (2) Lactose | 50 mg |
| (3) Corn starch | 88 mg |
| (4) Hydroxy propyl cellulose | 10 mg |
| (5) Magnesium stearate | 2 mg |
| | 200 mg/capsule |

TAN-1057C (15 mg) obtained by Example 6 was dissolved in 1N-NaOH (15 ml), allowed to stand for 10 min, and adjusted to pH 5.0. Inorganic salts in the solution were removed by means of a desalting appliance (Microacylizer G1, manufactured by Asahikasei). The desalted solution was concentrated, lyophilized to give a powder (17 mg) containing TAN-1057A and B. This powder (17 mg) was subjected to a prep. HPLC [column: YMC PAK AM-324 ODS, mobile phase: 0.01M phosphate buffer (pH 5.0)]. The bioactive fractions were desalted by the desalting appliance mentioned above, followed by concentration. The concentrate was lyophilized to give an equilibrium mixture (8 mg) of TAN-1057A and B. The physiochemical properties of the compound were consistent with those of the authentic sample.

EXAMPLE 9

The above ingredients (1), (2), (3) and (4) are mixed and granulated by a conventional method. To the granules is added the ingredient (5). The mixture is packed into a gelatine capsule No.1 (according to the Pharmacopeia of Japan, Tenth Edition).

EXAMPLE 10

Injection

TAN-1057A and B (5 g, equilibrium mixture}1 is dissolved in 1l of distilled water, in which is dissolved 100 g of mannitol. After filtration 2 ml each portion of the filtrate is filled into ampoules. The solution in the ampoules is freeze-dried and sealed to give ampoules for extemporaneous use. When the injection is administered, the ampoule is opened and the drug is dissolved in 2 ml of physiological saline solution, then the solution is injected subcutaneously, intravenously or intramuscularly.

EXAMPLE 11

| Capsule | |
|---|---|
| (1) TAN-1057A | 50 mg |
| (2) Lactose | 50 mg |
| (3) Corn starch | 88 mg |
| (4) Hydroxy propyl cellulose | 10 mg |
| (5) Magnesium stearate | 2 mg |
| | 200 mg/capsule |

The above ingredients (1), (2), (3) and (4) are mixed and granulated by a conventional method. To the granules is added the ingredient (5). The mixture is packed into a gelatine capsule No.1 (according to the Pharmacopeia of Japan, Tenth Edition).

EXAMPLE 12

Injection

TAN-1057A is dissolved in 1 l of distilled water, in which is dissolved 100 g of mannitol. The solution is subjected to filtration, and 2 ml each portion of the filtrate is filled into ampoules. The solution in the ampoules is freeze-dried and sealed to give ampoules for extemporaneous use. When the injection is administered, the ampoule is opened and the drug is dissolved in 2 ml of physiological saline solution, then the solution is injected subcutaneously, intravenously or intramuscularly.

What we claim is:

1. A compound of the formula:

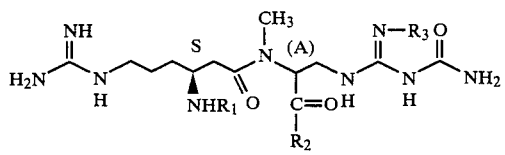

wherein, the absolute configuration at (A) is R or S; R1 is hydrogen and both R2 and R3 taken together form a chemical bond, or R3 is hydrogen, both R1 and R2 taken together form a chemical bond; and pharmaceutically acceptable salts thereof.

2. The compound according to claim 1, wherein R1 is hydrogen, both R2 and R3 taken together form a chemical bond, and the absolute configuration at (A) is S.

3. The compound according to claim 1 wherein R1 is hydrogen, both R2 and R3 taken together form a chemical bond, and the absolute configuration, at (A) is R.

4. The compound according to claim 1, wherein R3 is hydrogen, both R1 and R2 taken together form a chemical bond, and the absolute configuration at (A) is R.

5. The compound according to claim 1, wherein R3 is hydrogen, both R1 and R2 taken together form a chemical bond, and the absolute configuration at (A) is S.

6. An antibacterial agent which comprises an effective amount of at least one species of compounds represented by the formula:

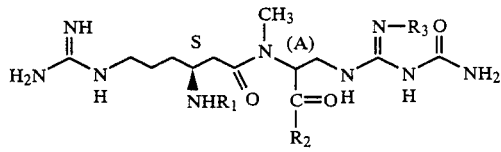

wherein, the absolute configuration at (A) is R or S; R1 is hydrogen and both R2 and R3 taken together form a chemical bond, or R3 is hydrogen and both R1 and R2 taken together form a chemical bond; or pharmaceutically acceptable salts thereof and a pharmacologically acceptable carrier.

7. An antitumor agent for inhibiting the growth of tumorous cells which comprises an effective amount of at least one species of compounds represented by the formula:

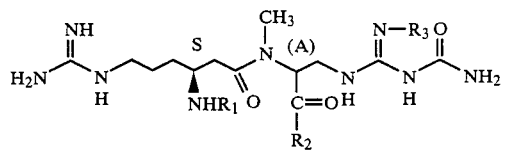

wherein, the absolute configuration at (A) is R or S; R1 is hydrogen and both R2 and R3 taken together form a chemical bond, or R3 is hydrogen and both R1 and R2 taken together form a chemical bond; or pharmacologically acceptable salts thereof and a pharmacologically acceptable carrier.

* * * * *